United States Patent [19]

Ahmed

[11] Patent Number: 5,362,758
[45] Date of Patent: Nov. 8, 1994

[54] OPHTHALMIC PIROXICAM SOLUTION

[75] Inventor: Imran Ahmed, New York, N.Y.

[73] Assignee: Pfizer Inc., New York, N.Y.

[21] Appl. No.: 970,350

[22] Filed: Oct. 30, 1992

Related U.S. Application Data

[63] Continuation of Ser. No. 584,227, Sep. 18, 1992, abandoned.

[51] Int. Cl.$^5$ ............................................. A61K 31/74
[52] U.S. Cl. ..................... 514/777; 514/781; 514/912; 514/914; 514/915; 424/427; 424/48
[58] Field of Search ................ 424/427, 428, 78.04; 514/912, 914, 915, 777, 781

[56] References Cited

U.S. PATENT DOCUMENTS

| | | | |
|---|---|---|---|
| 3,591,584 | 7/1971 | Lombardino | 260/243 |
| 4,470,965 | 9/1984 | Wolf et al. | 514/597 |
| 4,474,811 | 10/1984 | Masuda et al. | 514/570 |
| 4,678,666 | 7/1986 | Nozawa et al. | 424/81 |
| 4,688,053 | 12/1986 | Fries | 514/222 |

FOREIGN PATENT DOCUMENTS

| | | |
|---|---|---|
| 899587 | 8/1984 | Belgium . |
| 0336200 | 3/1989 | European Pat. Off. . |
| 62-142116 | 6/1987 | Japan . |

*Primary Examiner*—Thurman K. Page
*Assistant Examiner*—C. Azpuru
*Attorney, Agent, or Firm*—Peter C. Richardson; Paul H. Ginsburg; Seymour G. Bekelnitzky

[57] ABSTRACT

Aqueous solutions for treating inflammations of the eye, comprising: from about 0.03–3 weight percent of piroxicam; an effective amount of a buffer; from about 0 to about 1 weight percent of a wetting agent; from about 0 to about 5 weight percent of a pH adjusting agent; from about 0 to about 5 weight percent of a tonicity agent; an effective amount of a preservative; from about 0 to about 3 weight percent of a demulcent polymer; from about 0 to about 40 weight percent of a complexing agent; and from about 0 to about 0.1 weight percent of a stabilizer; and having a pH between about 7 and about 10.

14 Claims, No Drawings

OPHTHALMIC PIROXICAM SOLUTION

This is a continuation, of application Ser. No. 07/584,227, filed on Sep. 18, 1992 now abandoned.

BACKGROUND OF THE INVENTION

This invention relates to aqueous piroxicam solutions useful in the treatment of inflammations of the eye such as allergic conjunctivitis, edemas, acute uveitis, ocular trauma, scleritis and keratoconjunctivitis.

Piroxicam, the chemical name of which is N-(2-pyridyl)-2-methyl-4-hydroxy-2H-1,2-benzothiazine-3-carboxamide 1,1-dioxide, is a nonsteroidal anti-inflammatory agent. It is described and claimed in U.S. Pat. No. 3,591,584.

Several piroxicam containing pharmaceutical compositions for uses other than ophthalmic administration are known. U.S. Pat. No. 4,688,053 refers to injectable solutions containing piroxicam. U.S. Pat. No. 4,678,666 refers to piroxicam containing gels for dermatological administration. Japanese Patent Application Disclosure 62-142116 refers to piroxicam containing suppositories.

Aqueous piroxicam suspensions for ophthalmic use are also known. Belgian patent 899,587 refers to an anti-inflammatory eye lotion that is a suspension of piroxicam in an aqueous, sterile, hypertonic solution.

In the ophthalmic compositions of the present invention, piroxicam, the active ingredient, is dissolved in an aqueous solution, facilitating administration of the drug, accuracy in dosing and patient toleration. The fact that the active ingredient is dissolved in solution also prevents blurring and causes such compositions to be faster acting than suspensions of piroxicam.

The aqueous piroxicam solutions of the present invention also exhibit substantially greater stability than the aqueous piroxicam suspensions. They need not be nitrogen purged during preparation and storage. The stability inherent in the novel solutions of this invention may be further enhanced by packaging them in containers capable of blocking transmission of light having a wavelength in the range from about 290 nm to about 550 nm.

SUMMARY OF THE INVENTION

The present invention relates to aqueous solutions for treating inflammations of the eye comprising: from about 0.03 to about 3 weight percent of piroxicam; an effective amount of a buffer; from about 0 to about 1 weight percent of a wetting agent; from about 0 to about 5 weight percent of a pH adjusting agent; from about 0 to about 5 weight percent of a tonicity agent; an effective amount of a preservative; from about 0 to about 3 weight percent of a demulcent polymer; from about 0 to about 40 weight percent of a complexing agent; and from about 0 to about 0.1 weight percent of a stabilizer; and having a pH between about 7 and about 10. These solutions are hereinafter referred to as solutions having Formulation I. The solutions having Formulation I are useful in the treatment of inflammations of the eye such as allergic conjunctivitis, edemas, acute uveitis, ocular trauma, scleritis and keratoconjunctivitis.

The present invention also relates to a method of treating inflammatory diseases of the eye such as allergic conjunctivitis, edemas, acute uveitis, ocular trauma, scleritis and keratoconjunctivitis in a mammal, including a human, comprising administering to a mammal in need of such treatment an anti-inflammatory effective amount of a solution having Formulation I.

The present invention also relates to a container comprising a packaging material capable of blocking the transmission of light having a wavelength from about 290 nanometers to about 550 nanometers, said container having therein a solution having Formulation I.

DETAILED DESCRIPTION OF THE INVENTION

In a preferred embodiment of this invention, the solution having Formulation I is an aqueous isotonic solution comprising: from about 0.03 to about 3 weight percent piroxicam; from about 0.5 to about 1 weight percent boric acid; from about 0.5 to about 1 weight percent sodium borate decahydrate; from about 0.4 to about 1 weight percent glycerin; from about 0.04 to about 1 weight percent polyethylene glycol 300 (PEG 300); from about 0.004 to about 0.01 weight percent thimerosal; and from about 0.03 to about 0.3 weight percent sodium hydroxide.

In a more preferred embodiment of this invention, the solution having Formulation I is an isotonic aqueous solution comprising: about 0.3 weight percent piroxicam; about 0.67 weight percent boric acid; about 0.21 weight percent sodium borate decahydrate; about 1.0 weight percent glycerin; about 1.0 weight percent PEG 300; about 0.004 weight percent thimerosal; and about 0.11 weight percent sodium hydroxide.

Wetting agents, demulcent polymers, and complexing agents may be optionally added to the solutions having Formulation I without compromising efficacy or stability.

Buffers that may be employed in the present invention include: boric acid and borate salts such as sodium borate; carbonate salts such as sodium carbonate and potassium carbonate. Boric acid/sodium borate decahydrate is preferred. An effective amount of a buffer is generally from about 0.05 weight percent to about 10 weight percent.

Tonicity agents that may be employed in the present invention include propylene glycol, PEG 300, polyethylene glycol 400 (PEG 400), glycerin, polysorbate, sorbitol, dextran 40 and dextran 70. Preferably the tonicity agent comprises one or both of PEG 300 and glycerin.

Examples of preservatives that may be employed include thimerosal, phenylmercuric acetate and phenylmercuric nitrate, with thimerosal being preferred. An effective amount of a preservative is generally from about 0.001 weight percent to about 0.75 weight percent.

Demulcent polymers may optionally be added to the solutions of Formulation I. Because of their ability to hold large amounts of water, they are useful for coating and thus moisturizing the cornea of the eye. Cellulose derivatives, Dextran 40, Dextran 70, gelatin and liquid polyols are among the demulcent polymers suitable for use with this invention.

Wetting agents such as polysorbates, poloxamer, tyloxapol and lecithin may also optionally be added to the solutions of Formulation I to optimally wet the surface of the eye.

The solutions having Formulation I have a pH of between about 7 and about 10. To maintain the pH of these solutions, pH adjusting agents may be added. Examples of suitable pH adjusting agents include: a) mineral acids such as sulfuric acid, nitric acid and phosphoric acid; b) alkali salts such as sodium and potassium hydroxide; and c) organic acids such as acetic and citric acids.

Complexing agents may also optionally be added to solutions having Formulation I to facilitate the dissolution of greater amounts of piroxicam. These are especially useful in solutions having a piroxicam concentration greater than 0.3 weight percent. Cyclodextrins and soluble cyclodextrin derivatives may be used for this purpose.

The water used in solutions having Formulation I is generally sterilized, and is peferably distilled and deionized.

The stability of the solutions having Formulation I is enhanced by storing them in a container comprising a packaging material that is capable of blocking the transmission of light having a wavelength from about 290 nanometers to about 550 nanometers. In a preferred embodiment of this invention, a solution having Formulation I is stored in an opaque low density polyethylene bottle having low density polyethylene dropper tips and a polypropylene cap.

The ophthalmic piroxicam solutions of the present invention are administered topically by applying them to the cul-de-sac of the eye from a dropper controlled bottle or dispenser. A typical dose regimen for an adult human may range from about 2 to about 8 drops per day (about 0.3 mg to about 1.2 mg piroxicam for a 0.3 weight percent piroxicam solution). Dosages for adult humans may, however, be as high as about 20 mg piroxicam per day (133 drops per day).

The following examples illustrate but do not limit the scope of this invention.

EXAMPLE 1

A 0.03 weight percent ophthalmic piroxicam solution was prepared by dissolving 67.0 g (0.67 weight percent) boric acid, 20.7 g (0,207 weight percent) sodium borate decahydrate, 100.0 g (1.0 weight percent) glycerin, 100.0 g of polyethylene glycol 300 (1.0 weight percent), and 0.40 g (0.004 weight percent) thimerosal into approximately 8000 g of deionized, distilled water. The pH of the solution was brought to 7.9 by the addition of an appropriate amount of an 8 weight percent stock solution of sodium hydroxide. Piroxicam, 3.0 g, was dissolved into the above vehicle with agitation. The vehicle pH was re-adjusted to pH 7.9 by the addition of an 8 weight percent stock solution of sodium hydroxide. A total of approximately 5 g of sodium hydroxide was required to adjust the pH, resulting in a concentration of 0.05 weight percent sodium hydroxide in the formulation. The final batch weight was brought to 10,000 g with the addition of the required amount of water. This formulation was then passed through a 0.2 micron sterilizing filter, and held there for filling.

EXAMPLE 2

A 0.10 weight percent ophthalmic piroxicam solution was prepared by dissolving 67.0 g (0.67 weight percent) boric acid, 20.7 g (0.207 weight percent) sodium borate decahydrate, 100.0 g (1.0 weight percent) glycerin, 100.0 g of polyethylene glycol 300 (1.0 weight percent), and 0.40 g (0.004 weight percent) thimerosal into approximately 8000 g of deionized, distilled water. The pH of the solution was brought to 8.2 by the addition of an appropriate amount of an 8 weight percent stock solution of sodium hydroxide. Piroxicam, 10.0 g, was dissolved into the above vehicle with agitation. The vehicle pH was re-adjusted to pH 8.2 by the addition of an 8 weight percent stock solution of sodium hydroxide. A total of approximately 8 g of sodium hydroxide was required to adjust the pH, resulting in a concentration sodium hydroxide in the formulation. The final batch weight was brought to 10,000 g with the addition of the required amount of water. This formulation was passed through a 0.2 micron sterilizing filter, and held there for filling.

EXAMPLE 3

A 0.30 weight percent ophthalmic piroxicam solution was prepared by dissolving 67.0 g (0.67 weight percent) boric acid, 20.7 g (0.207 weight percent) sodium borate decahydrate, 100.0 g (1.0 weight percent) glycerin, 100.0 g of polyethylene glycol 300 (1.0 weight percent), and 0.40 g (0.004 weight percent) thimerosal into approximately 8000 g of deionized, distilled water. The pH of the solution was brought to 8.6 by the addition of an appropriate amount of an 8 weight percent stock solution of sodium hydroxide. Piroxicam, 30.0 g, was dissolved into the above vehicle with agitation. The vehicle pH was re-adjusted to pH 8.6 by the addition of an 8 weight percent stock solution of sodium hydroxide. A total of approximately 21 g of sodium hydroxide was required to adjust the pH, resulting in a concentration of 0.21 weight percent sodium hydroxide in the formulation. The final batch weight was brought to 10,000 g with the addition of the required amount of water. This formulation was passed through a 0.2 micron sterilizing filter, and held for filling.

EXAMPLE 4

The following package was used to contain the solution of Example 1.

| Component | Description |
|---|---|
| Amber bottle | Low density polyethylene with a metallic oxide brown color concentrate and a tinuvin ultraviolet (UV) inhibitor |
| Dropper tips | White low density polyethylene |
| Cap | White polypropylene with a zinc sulfide color concentrate and a UV inhibitor |

I claim:
1. An aqueous solution for treating inflammations of the eye comprising: from about 0.03–3 weight percent of piroxicam; a buffer comprising from about 0.5 to about 1 percent by weight of boric acid and from about 0.5 to about 1 percent by weight of sodium borate; from about 0 to about 1 weight percent of a wetting agent; from about 0 to about 5 weight percent of a pH adjusting agent; from about 0 to about 5 weight percent of a tonicity agent; an effective amount of a preservative; from about 0 to about 3 weight percent of a demulcent polymer; from about 0 to about 40 weight percent of a complexing agent; and from about 0 to about 0.1 weight percent of a stabilizer; and having a pH between about 7 and about 10.

2. A solution according to claim 1, wherein the preservative is selected from the group consisting of thimerosal, phenyl mercuric acetate and phenyl mercuric nitrate.

3. A solution according to claim 1, comprising from about 0.4 to about 1 weight percent glycerin; from about 0.04 to about 1 weight percent polyethylene glycol 300; from about 0.4 to about 1 weight percent thimerosal; and from about 0.03 to about 0.3 weight percent sodium hydroxide.

4. A solution according to claim 1, comprising: about 0.3 weight percent piroxicam; about 0.67 weight percent boric acid; about 0.21 weight percent sodium borate decahydrate; about 1.0 weight percent glycerin; about 1.0 weight percent polyethylene glycol 300; about 0.004 weight percent thimerosal; and about 0.11 weight percent sodium hydroxide.

5. A solution according to claim 1, wherein said solution comprises about 3 grams piroxicam, about 60 grams boric acid, about 21 grams sodium borate, about 100 grams glycerin and about 100 grams PEG 300, and wherein said solution has a pH of about 8 and the total weight of the solution is about 10,000 grams.

6. A solution according to claim 1, wherein the wetting agent is selected from the group consisting of polysorbates poloxamer, tyloxapol and lecithin.

7. A solution according to claim 1, wherein the tonicity agent is selected from the group consisting of glycerin, polyethylene glycol 300, propylene glycol, polyethylene glycol 400, polysorbate, Dextran 40 and dextran 70 and mixture thereof.

8. A solution according to claim 2, wherein the preservative is thimerosal.

9. A solution according to claim 1, wherein the demulcent polymer is selected from the group consisting of cellulose, dextran 40, dextran 70, gelatin and liquid polyols.

10. A solution according to claim 1, wherein the complexing agent is cyclodextrin.

11. A solution according to claim 1, wherein the stabilizer is selected from sodium EDTA and sodium bisulfite.

12. A solution according to claim 1, wherein the pH adjusting agent is selected from organic acids, mineral acids and alkali bases.

13. A method of treating an inflammation of the eye in a mammal, comprising administering to a mammal in need of such treatment an anti-inflammatory effective amount of a solution according to claim 1.

14. A solution according to claim 1, wherein the tonicity agent is a mixture of glycerin and a poly(ethylene glycol).

* * * * *